United States Patent
Tai et al.

(12) 
(10) Patent No.: US 6,825,539 B2
(45) Date of Patent: Nov. 30, 2004

(54) INTEGRATED CIRCUIT-INTEGRATED FLEXIBLE SHEAR-STRESS SENSOR SKIN AND METHOD OF FABRICATING THE SAME

(75) Inventors: Yu-Chong Tai, Pasadena, CA (US); Yong Xu, Royal Oak, MI (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 10/403,732

(22) Filed: Mar. 31, 2003

(65) Prior Publication Data

US 2003/0199116 A1 Oct. 23, 2003

Related U.S. Application Data

(60) Provisional application No. 60/367,133, filed on Apr. 1, 2002.

(51) Int. Cl.$^7$ .............................................. H01L 21/00
(52) U.S. Cl. ....................................... 257/417; 257/420
(58) Field of Search ................................. 257/414–420

(56) References Cited

U.S. PATENT DOCUMENTS 6,071,819 A * 6/2000 Tai et al. ..................... 438/694

* cited by examiner

*Primary Examiner*—H. Jey Tsai
(74) *Attorney, Agent, or Firm*—Daniel L. Dawes; Myers Dawes Andras & Sherman LLP (57) ABSTRACT

An IC-integrated, flexible, shear-stress sensor skin is made by providing a wafer with integrated circuits and sensor elements which are fabricated in the wafer, disposing a first polymer layer on the wafer and sensor elements to provide mechanical support for the sensor elements, defining a cavity below the sensor elements to provide thermal isolation, while the sensor element remains supported by the first polymer layer, and isolating the sensor elements into a plurality of islands defined in the wafer, so that the islands, with at least one sensor element on at least one of the islands, and the integrated circuits form the IC-integrated, flexible, shear-stress sensor skin. The invention is an IC-integrated, flexible, sensor skin made according to the method.

12 Claims, 6 Drawing Sheets

INTEGRATED CIRCUIT-INTEGRATED FLEXIBLE SHEAR-STRESS SENSOR SKIN AND METHOD OF FABRICATING THE SAME

RELATED APPLICATIONS

The present application is related to U.S. Provisional Patent Application Ser. No. 60/367,133, filed on Apr. 1, 2002, which is incorporated herein by reference and to which priority is claimed pursuant to 35 USC 119.

BACKGROUND OF THE INVENTION

1. Field of the Invention

The invention relates to MEMS devices combined with integrated circuits, particularly as used as biomedical sensors and devices.

2. Description of the Prior Art

Since the emergence of MEMS technology, numerous miniaturized sensors and actuators have been fabricated using techniques originally developed for the integrated circuits industry. Inherently, most MEMS devices are built on rigid substrates. However, for a wide variety of applications, it has long been desirable for sensors, actuators and circuits to be mounted on non-planar surfaces or even on flexible objects such as a human body.

For example, the inventors of the present application have done work on a new way of controlling the Unmanned Aerial Vehicle (UAV) through the sensing/controlling of the flow separation at the leading edge. This requires distributed sensors mounted on the cylindrical surface of leading edge. Accordingly, the inventors have developed flexible shear-stress sensor skins for the UAV project. See F. Jiang et. al., "*Flexible Shear Stress Sensor Skin For Aerodynamics Applications*," presented at IEEE International Conference on Micro Electro Mechanical Systems (MEMS), Miyazaki, Japan, 2000.

These skins, however, contained only sensors and required many electrical lead connections. The complete separation-detecting system consisted of the packaged sensor skins, bias board, and data acquisition board and a tremendous number of interconnection cables.

In particular, what is needed for a shear-stress sensor skin, with on-skin bias circuits, amplifiers, and multiplexers, is a design that allows elimination of the bias board and interconnection cables, simplification of the design of the data acquisition board, and improvement system reliability at the same time.

Therefore, what is needed is some kind of design that allows integration with these circuits, since this integration promises to bring very important benefits such as operational improvement, packaging simplification and cost reduction.

BRIEF SUMMARY OF THE INVENTION

The invention is directed to a new device called an IC-integrated, flexible, shear-stress sensor skin or MEMS skin. By integrating both bias and signal-conditioning circuitry on-chip, the wiring of the MEMS skin 10 is significantly simplified and reliability is improved. The circuit is first made by a commercial IC foundry and micromachining is done on the CMOS wafers to form the skins. In the illustrated embodiment, the use of the sensor skin is demonstrated by packaging it on a semi-cylindrical aluminum block and tested it in a wind tunnel.

In the illustrated embodiment, the skin has successfully identified both the flow separation and stagnation points. It is believed that the IC integrated skin can be applied to many applications in biomedicine, wearable microsystems, and robotics to mention only a few. The illustrated embodiment may thus be modified according to the intended application without departing from the scope of the invention.

The IC-integrated skin technology demonstrated in this invention has many applications. The first example is for the biomedical applications. Many MEMS devices have already been widely employed in biomedicine where miniaturized sensors, actuators and other microstructures are needed. However, the IC integrated skins advance the art to another level of functionality. The sensor skin can be mounted on human body like a bandage. Examples for future applications may include skins with sensors capable of monitoring physiological parameters such as glucose and insulin levels. For implantable applications, sensors can be built on flexible substrates to conform to the organ shape or to minimize tissue trauma during patient movement. Skins incorporating arrays of tactile, temperature, and other sensors are very helpful to surgical instruments for minimally invasive surgery. The IC-integrated skin is also of great promise for wearable microsystems, robotics and many other research areas. In this invention, Parylene is used as skin material. However, other polymers can also be used to meet the specific requirements of the application.

More specifically, the invention is a method of fabricating an IC-integrated, flexible, shear-stress sensor skin comprising the steps of providing a wafer with integrated circuits and sensor elements coupled thereto, both of which integrated circuits and sensor elements are fabricated in or on the wafer; disposing a first polymer layer on the wafer and on the sensor elements, the first polymer layer providing mechanical support for the sensor elements; defining a cavity below each of the sensor elements to release the sensor elements from the wafer to provide thermal isolation therefrom, while the sensor element remains supported by the first polymer layer; and isolating the sensor elements into a plurality of islands defined in the wafer, so that the islands, at least one with at least one sensor element, and the integrated circuit elements coupled thereto form the IC-integrated, flexible, shear-stress sensor skin.

The step of disposing a first polymer layer on the wafer and on the sensor elements comprises disposing two polymers layers on the wafer and on the sensor elements to form a compound layer, wherein at least one of the two layers is chosen of a material suited for use with the sensor elements.

The step of disposing two polymers layers on the wafer and on the sensor elements to form a compound layer comprises disposing a first of the two polymer layers to form a mechanical support for the islands and disposing a second of the two polymer layers to form a diaphragm support for the sensor elements.

The step of disposing a first of the two polymer layers to form a mechanical support for the islands and disposing a second of the two polymer layers to form a diaphragm support for the sensor elements comprises disposing a Parylene C layer as the first of the two polymer layers to form a mechanical support for the islands and disposing a Parylene N layer as the second of the two polymer layers to form a diaphragm support for the sensor elements.

The first polymer layer is disposed on a first side of the wafer and the method further comprises the step of disposing a second polymer layer on an opposing second side of the wafer to encapsulate the islands between the first and second polymer layers.

The method further comprises the step of thinning the wafer.

The step of isolating the sensor elements into a plurality of islands defined in the wafer comprises defining the islands in the wafer by deep reactive ion etching regions of the wafer containing at least one sensor element.

The step of providing a wafer with integrated circuits and sensor elements coupled thereto comprises providing biasing or signal conditioning circuits adapted for the sensor elements among the integrated circuits provided in the wafer.

The step of providing a wafer with integrated circuits and sensor elements coupled thereto comprises providing a multiplexer for selectively accessing a plurality of the sensor elements on the skin.

The step of disposing a second polymer layer on a side of the wafer to encapsulate the islands between the first and second polymer layers comprises disposing a Parylene C layer as the second polymer layer on the opposing side.

The invention also includes an apparatus or an IC-integrated, flexible, shear-stress sensor skin fabricated by the foregoing methods or otherwise having the resulting structure realized by the fabrication. Namely, the apparatus comprises: a wafer defined into a plurality of islands; at least one integrated circuit fabricated in or on the wafer; at least one sensor element fabricated in or on at least one island and coupled to the integrated circuit; a first polymer layer disposed on the wafer and on the sensor element, the first polymer layer providing mechanical support for the sensor element and islands; and a cavity defined in the island below each sensor element to provide thermal isolation from the island, while the sensor element remains supported by the first polymer layer, so that the islands, each with at least one sensor element, and the integrated circuit coupled thereto form the IC-integrated, flexible, shear-stress sensor skin.

While a shear-stress sensor is described above, the invention is more generally an IC-integrated, flexible sensor skin comprised of a wafer defined into a plurality of islands; at least one integrated circuit fabricated in or on the wafer; with none, one or more sensor elements fabricated in or on each island and coupled to the integrated circuit; a first flexible polymer layer disposed on a first side of the wafer and on the sensor element, the first polymer layer providing mechanical support for islands in at least the case where a shear-stress sensor is employed; a second flexible polymer layer on an opposing second side of the wafer to encapsulate the islands between the first and second polymer layers; and a cavity defined in the island below each sensor element to provide isolation from the island in at least the case where a shear-stress sensor is employed, while the sensor element remains supported by the first polymer layer, so that the islands, with at least one sensor element on at least one island, and the integrated circuit coupled thereto form the IC-integrated, flexible sensor skin. Any parameter may be measured by the sensor and not only shear stresses.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Generally speaking, MEMS-IC integration can be categorized into two groups: hybrid integration and monolithic integration. In the case of hybrid integration, MEMS parts and circuit parts are fabricated separately and then are packaged together by wafer bonding or other packaging technologies. With regard to flexible shear-stress sensor skin, monolithic integration is preferred in the present embodiment since hybrid integration does not simplify the packaging process.

Based on when MEMS parts are fabricated, monolithic integration can be classified as mixed MEMS-IC process, MEMS-first process (pre-IC or pre-CMOS) and IC-first process (post-IC or post-CMOS). The first approach is best exemplified by Analog Devices' accelerometer, which is fabricated by interleaving and customizing the MEMS manufacturing steps with the IC process. H. Smith et al. at Sandia National Laboratories developed a MEMS-first process. In this approach, MEMS devices are first fabricated in a trench on the surface of the wafer. The wafer is then planarized and the trench is sealed. The wafer with MEMS is then processed using conventional process.

However, it would be highly unlikely for any IC foundry service to modify their IC fabrication process or take pre-processed wafers. Therefore, most monolithic integration is done with the post-IC approach, taking advantages of the widely available CMOS foundry services. For IC-integrated shear-stress sensor skin 10 of the invention, post-CMOS process is chosen for the same reason. However, it is to be expressly understood that any form of MEMS-IC integration can be employed with appropriate modifications.

The measurement of shear stress is of great importance for many applications such as fluid dynamics monitoring, but obtaining it remains a difficult task largely due to the lack of instrumentation. There are many methods to measure local wall shear stress, including Stanton tube, direct measurement, thermal method, Preston tube, sub-layer fence and electrochemical technique. Of these approaches, the thermal method is most widely used since it does not interfere with the flow and it offers the possibility of measuring time-varying flows. Conventional thermal shear-stress sensors are typically made by depositing thin-film metal resistors, mostly platinum or nickel, on flat substrates. During operation, the resistor is electrically heated, while the fluid flow cools it down. The input power of the resistor will change with the wall shear stress from the ambient flow field and this change can be readily detected electronically. A large portion of the power is lost to the substrate via thermal conduction.

With micromachining technology, a vacuum cavity can be built underneath the resistor to reduce the heat loss to the substrate, thus improving the sensitivity and frequency response of sensor. The basic structure of the micromachined thermal shear stress sensor is a polysilicon resistor sitting on a nitride diaphragm with a vacuum cavity underneath. This is the sensor design used in the non-integrated sensor skin. See FIG. 1.

Figures 1, 2:
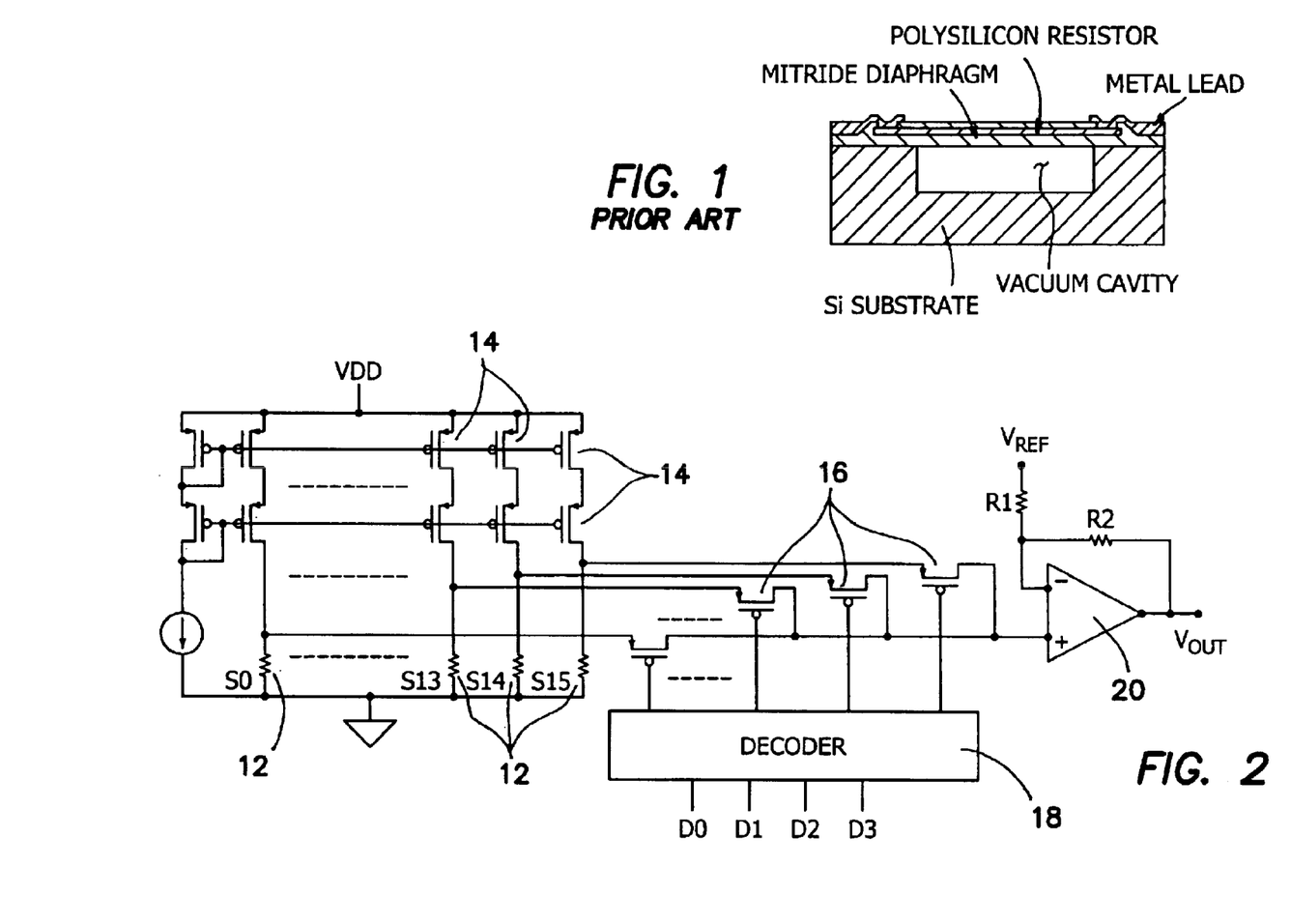
FIG. 1 is a simplified side cross-sectional view of a prior art shear-stress sensing element.
FIG. 2 is a schematic of a circuit diagram of a bias and signal conditioning circuit integrated onto the wafer on which the sensors are fabricated and which is connected to the sensors in an integrated fashion.
Figure 4A:
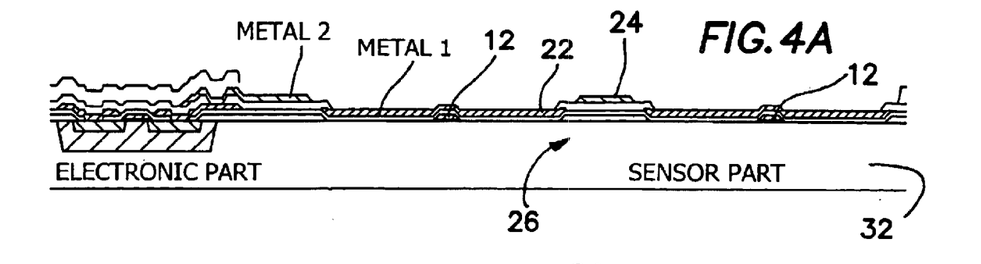
FIGS. 4a–4g are diagrammatic side cross-sectional views illustrating the method of the invention and the device fabricated from the method.
Figure 4B:
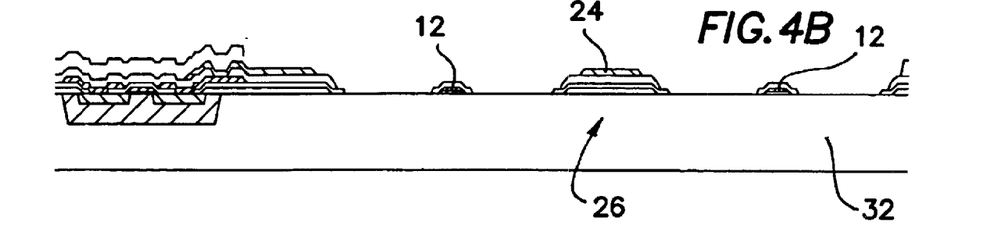
Figure 4C:
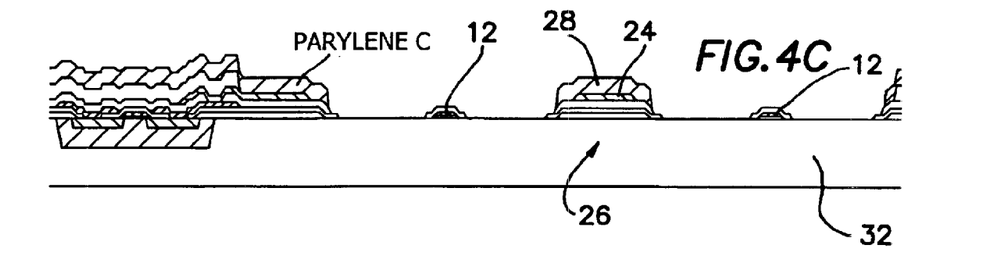

Due to the limitation of post-CMOS process, the structure of FIG. 1 cannot be practically employed in the illustrated embodiment. For IC-integrated skin 10 of the invention, the gate poly of the CMOS process is utilized as the sensing element of the shear stress sensor. The silicon underneath is etched away to achieve the thermal isolation and a Parylene N layer is deposited as diaphragm. The cross section of the sensor is illustrated in FIG. 4(g).

FIG. 2 shows the schematic of one embodiment of the integrated flexible shear-stress sensor skin 10. The shear-stress sensors 12, which utilize the gate polysilicon of the CMOS process as the sensing elements, operate in constant current (CC) mode and are biased by the cascode current mirrors 14. The output voltage is multiplexed by PMOS switches 16 and addressing circuitry 18. There are 16 shear stress sensors 12, which can be exactly accessed by a 4-bit address. An operational amplifier 20 is also implemented to perform on-chip amplification. The details of the schematic are not material to the invention and any one of a large number of different circuits could also be equivalently substituted for the schematic of FIG. 2.

Figure 3:
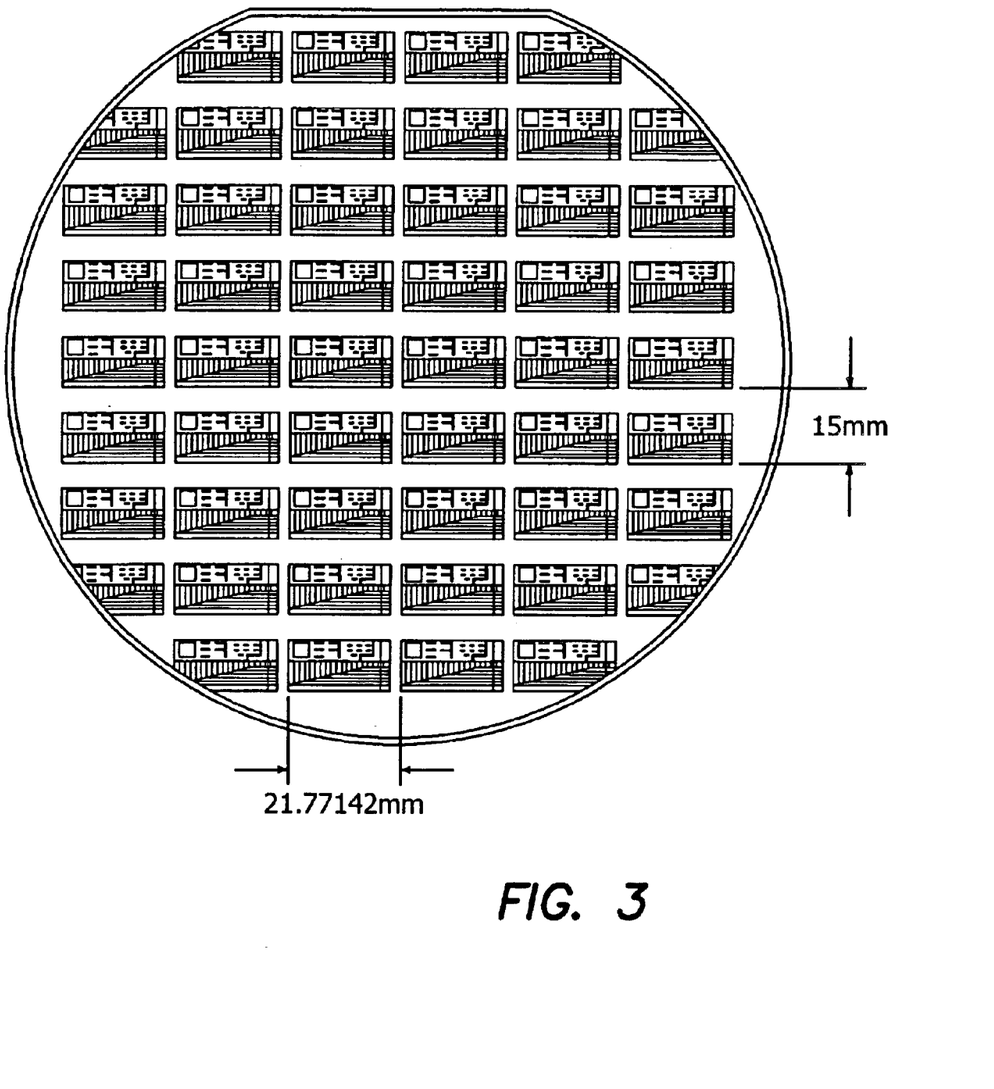
FIG. 3 is a photograph of the front side of a foundry wafer from which the devices of the invention are fabricated.

First, the circuits of FIG. 2 were fabricated by a conventional CMOS foundry. The gate poly of foundry process is 320 nm thick, with a temperature coefficient of resistance (TCR) of 0.1% and a sheet resistance of 20Ω per square. FIG. 3 shows a photograph of the 6" wafer from the foundry. The post-CMOS process was conducted at the Caltech Micromachining Lab. FIG. 4(a) shows the cross section of the wafer as produced by conventional foundry techniques. The polysilicon sensing elements 12 are covered by dielectric layers 22 and metal layers 24, so the process begins with patterning layers 22, 24 in the region of the sensor area 26 as suggested in FIG. 4b, followed by deposition and patterning of 10 $\mu$m Parylene C layer 28 on the front side of the wafer 32 as shown in FIG. 4c. Next, 1.5 82 m Parylene N layer 30 is deposited as shown in FIG. 4d.

Note that both Parylene C and N are used in this project. Parylene C serves as the mechanical support to encapsulate the silicon islands while Parylene N serves as the diaphragm material to support the sensing element after releasing. There are two major differences between Parylene C and N which lead to their different roles. The first difference lies in the melting temperature. Parylene N has a much higher melting temperature (420° C.) than that of Parylene C (290° C.). Since the polyresistor 12 will be heated up during operation, Parylene N is chosen as the membrane material to ensure the high temperature compatibility. The second difference lies in the deposition rate. Parylene C has a much higher deposition rate than Parylene N. To provide enough mechanical support, we need approximately 10 $\mu$m Parylene on both the front and back sides of the wafer 32. It is impractical to deposit such a thick layer of Parylene N.

Figure 4D:
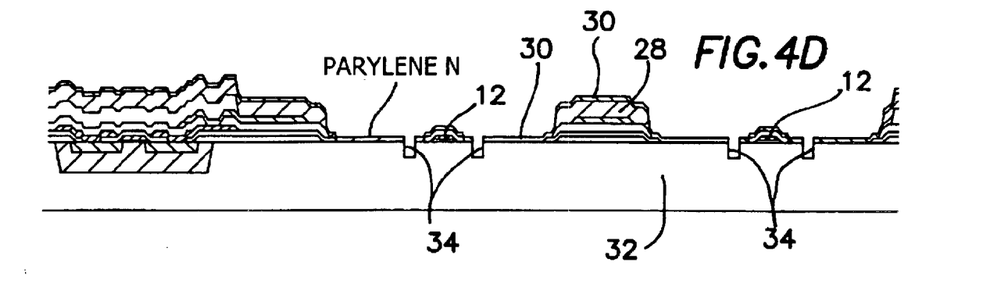

The releasing holes 34 for shear-stress sensor 12 are then formed by patterning Parylene N layer 30 as shown in FIG. 4(d). These holes 34 are further etched into the silicon substrate 32 to enhance the BrF$_3$ releasing process.

Figure 4E:
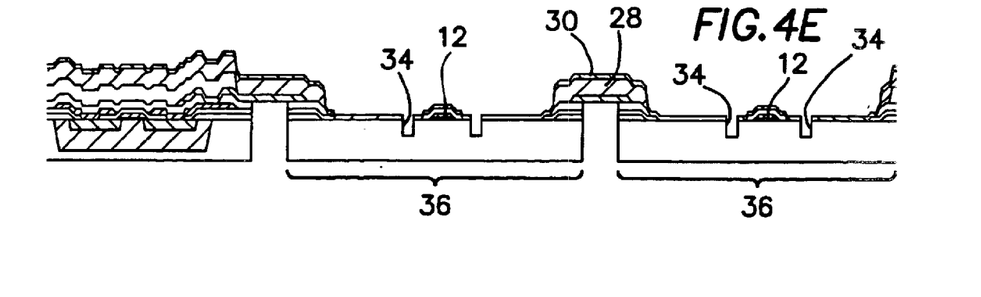

The process at the backside of wafer 32 begins with the thinning down of the wafer 32 as shown in FIG. 4e. Next the silicon islands 36 are formed by dry etching from the back side of wafer 32 as shown in FIG. 4e. Deep-reactive-ion-etching (DRIE) is used in these two steps.

Figure 4F:
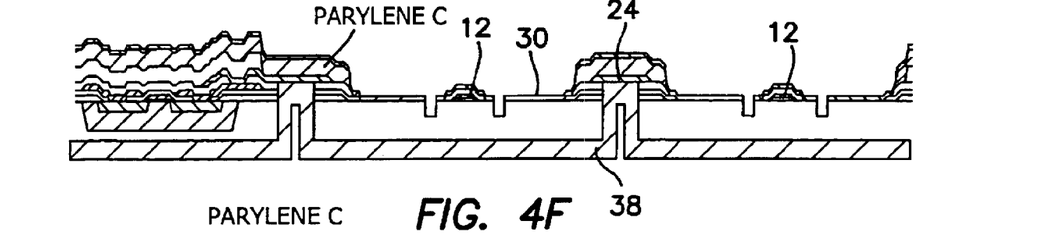
Figure 4G:
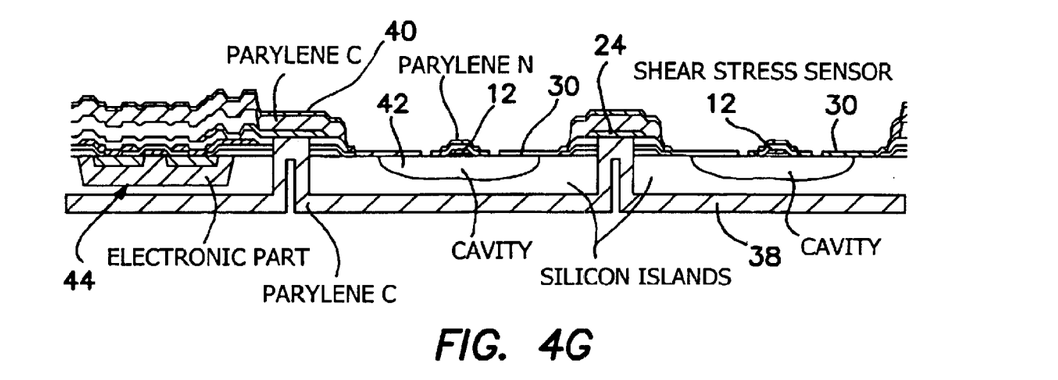
Figure 5:
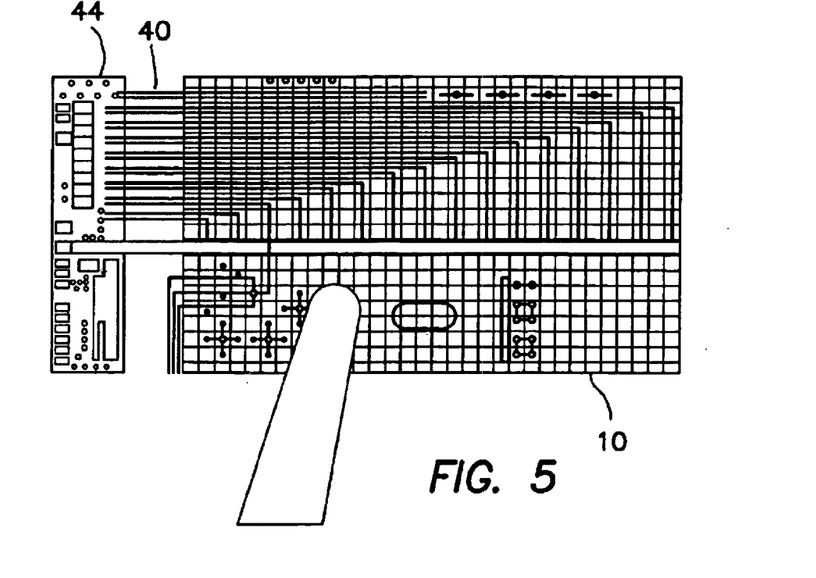
FIG. 5 is a photograph of the sensor skin fabricated from the method illustrated in FIGS. 4a–4g.

After selectively etching the silicon away from the backside of wafer 32 using DRIE to the dielectric layer 22 on the front side of wafer 32, pad etchant is used to remove the dielectric layer 22 itself thereby defining islands 36, which remain connected to each other through metal layers 24. Now a 10 $\mu$m Parylene C layer 38 is deposited on the back side of wafer 32 to sandwich the silicon islands 36 as shown in FIG. 4f. The final step is to release the polysilicon resistor or sensor 12 by BrF$_3$ gas phase etching as shown in FIG. 4g to create cavity 42 under sensor 12, which remains suspended on its Parylene N diaphragm. The purpose of this step is to achieve good thermal isolation for sensor 12. The integrated skin 10 cut from the wafer 32 is shown in the photograph of FIG. 5. The silicon islands 36 are clearly seen by shining light from the backside of the skin. The metal leads 40 going across the islands 36 from integrated circuits 44 can also be clearly observed.

Packaging

Figure 6:
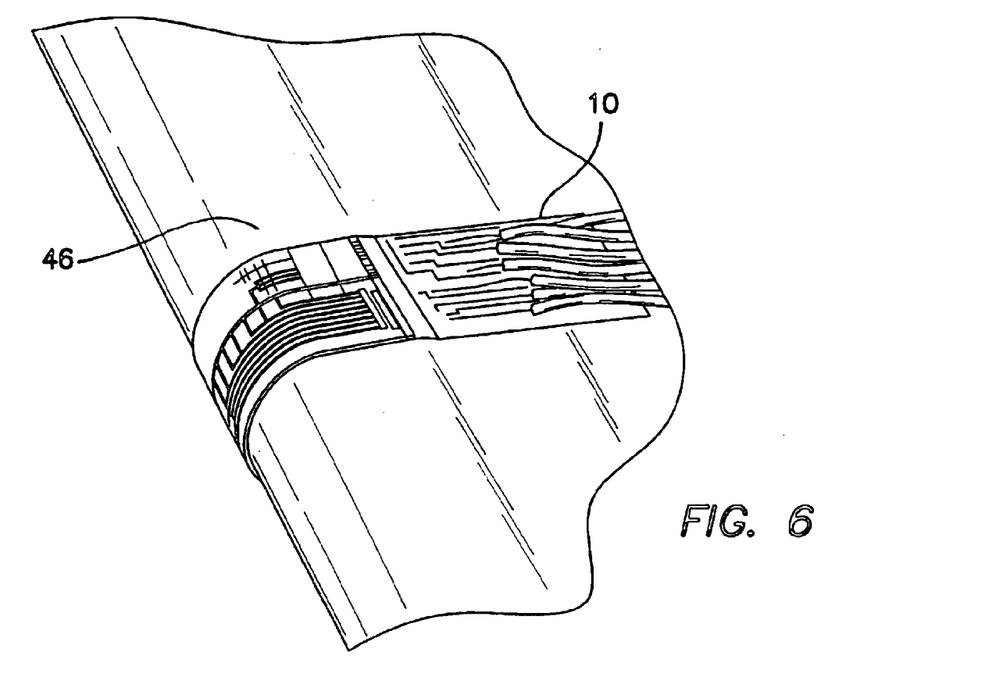
FIG. 6 is a photograph of the sensor skin of the invention attached to an air foil used to illustrate the operability of the device in a wind tunnel test.

The sensor skin 10 can be readily mounted on a non-planar surface. FIG. 6 shows a single skin 10 packaged on a semi-cylindrical surface of an aluminum block 46, which is the leading edge of an airfoil. Wire-bonding and conventional soldering were used to connect the sensor skin 10 to an outside instrument (not shown). This configuration is adequate for the wind tunnel test of the illustrated embodiment. However, for real aircraft wing applications, the edge of the skin that contains the metal pads should be folded underneath the wing surface.

Wind Tunnel Test

Figure 7:
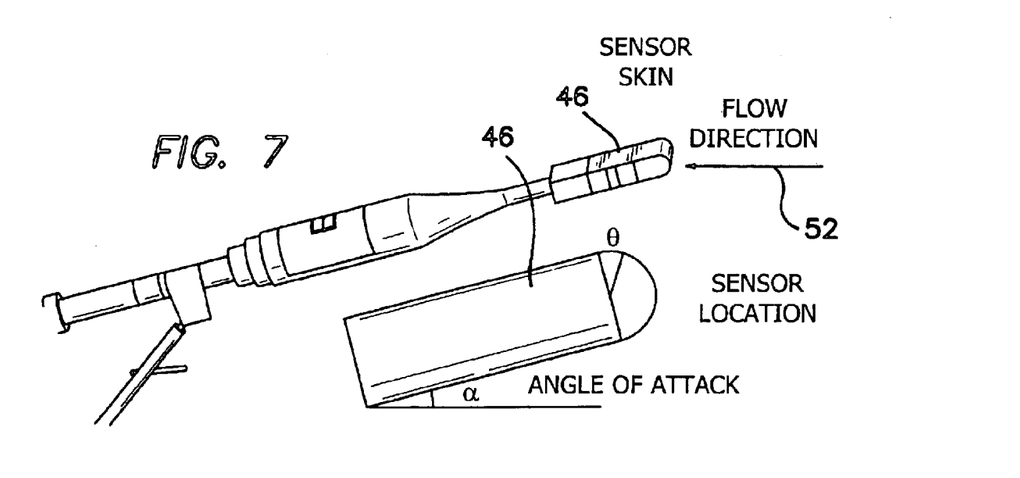
FIG. 7 is a photograph of the sensor skin of the invention attached to an air foil body for use in a wind tunnel test.

The wind tunnel test was carried out in the UCLA wind tunnel lab. The testing set-up is illustrated in FIG. 7 relative to a wind direction 52. The integrated sensor skin 10 was mounted on the top of the semi-cylindrical aluminum block 46. The definitions of sensor location θ and angle of attack α (AOA) are also shown diagramniatically in the inset in FIG. 7. Shear stress distributions at different angles of attack were measured using the on-chip circuitry as shown in FIG. 2. Sensor #0 is at the top surface and sensor #15 is at the bottom surface of the aluminum block 46. Since the angle between adjacent sensors is 12° and the 16 sensors exactly span 180°. It is worth noting that the vertical axis is the normalized output change ΔV/V, where V is the output voltage. The purpose of this normalization is to minimize the nonuniformity of the sensors' shear-stress sensitivity caused by the process variation.

Figure 8A:
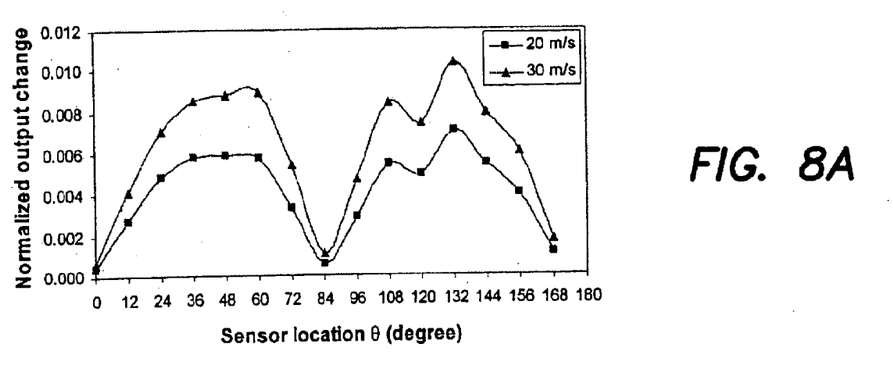
FIGS. 8a–8c are graphs of the data from the wind tunnel test of the device shown in FIG. 7 taken at 20 m/s and 30 m/s wind velocities showing the shift in separation point and stagnation point on the airfoil as a function of the angle of attack of the air foil as measured by the shear-stress sensor of the invention.

The steady-flow separation point 50, which is characterized theoretically by zero shear stress, can be observed. Interestingly, the stagnation point 48, where the shear stress has a minimum value in the middle, can also be identified. In the case of 0° angle of attack as shown in the graph of FIG. 8a for air velocities of 20 and 30 m/s, the stagnation point 48 is at the sensor #7 at 84°, which is exactly as expected. On the other hand, the separation points 50 are not present due to the small angle of attack.

Figure 8B:
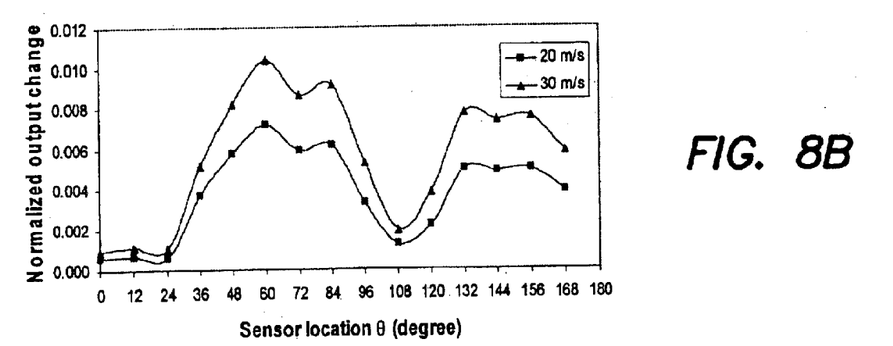
Figure 8C:
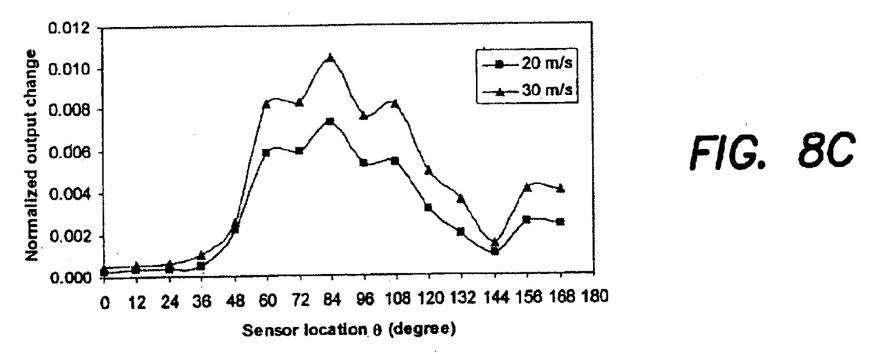

In the case of 15° angle of attack as shown in FIG. 8b, the separation point 50 is at sensor #2 at 24° while the stagnation point 48 is at sensor #9 at 108°. For 30° angle of attack as shown in FIG. 8c, the separation point 50 moves to sensor #3 at 36° while the stagnation point 48 moves to sensor #12 at 144°.

In summary, it can now be appreciated that an IC-integrated shear-stress sensor skin 10 has thus been successfully fabricated and demonstrated. With bias and signal conditioning circuitry 44 integrated on-chip, the packaging and deployment of the sensor skin 10 are significantly simplified and the system reliability is improved. In the wind tunnel test, both separation and stagnation points 50 and 48 are detected by the sensor skin 10. The IC-integrated smart skin technology demonstrated here has many other interesting applications.

The first example is for the biomedical applications. Many MEMS devices have already been widely employed in biomedicine where miniaturized sensors, actuators and other micro structures are needed. However, the IC-integrated smart skins 10 can further promote us to another level of functionality. The sensor skin 10 can be mounted on human body like a bandage. Examples for future applications may include smart skins 10 with sensors capable of monitoring physiological parameters such as glucose and insulin levels. For implantable applications, sensors can be built on flexible substrates to conform to the organ shape or to minimize tissue trauma during patient movement. Smart skins 10 incorporating arrays of tactile, temperature, and, other sensors will be very helpful for surgical instruments for minimally invasive surgery. The IC-integrated smart skin 10 would also be of great promise for wearable microsystems, robotics and many other research areas.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A monolithic IC-integrated, flexible, shear-stress sensor skin comprising:

a flexible supporting skin;

a wafer defined into a plurality of islands carried by the flexible supporting skin;

at least one integrated circuit fabricated in or on the wafer carried by the flexible supporting skin;

an integrated electrical coupling connected to the integrated circuit;

at least one integrated sensor element fabricated in or on each island during the same fabrication process as the integrated circuit, carried by the flexible supporting skin and coupled to the integrated circuit through the integrated electrical coupling;

a first polymer layer disposed on the wafer and on the sensor element, the first polymer layer providing mechanical support for the sensor element and islands; and a cavity defined in the island below each sensor element to provide thermal isolation from the island, while the sensor element remains supported by the first polymer layer, whereby the islands, each with at least one sensor element, and the integrated circuit coupled thereto form the IC-integrated, flexible, shear-stress sensor skin.

2. The sensor of claim 1 where the first polymer layer comprises two polymer layers forming a compound layer, wherein at least one of the two layers is chosen of a material suited for use with the sensor elements.

3. The sensor of claim 2 where the two polymers layers comprise a first of the two polymer layers to form a mechanical support for the islands and a second of the two polymer layers to form a diaphragm support for the sensor elements.

4. The sensor of claim 3 where a first of the two polymer layers and a second of the two polymer layers comprises a Parylene C layer as the first of the two polymer layers forming a mechanical support for the islands and a Parylene N layer as the second of the two polymer layers forming a diaphragm support for the sensor elements.

5. The sensor of claim 1 where the first polymer layer is disposed on a first side of the wafer and further comprising a second polymer layer on an opposing second side of the wafer to encapsulate the islands between the first and second polymer layers.

6. The sensor of claim 1 where the plurality of islands defined in the wafer are defined by deep reactive ion etching regions of the wafer containing at least one sensor element.

7. An IC-integrated, flexible, shear-stress sensor skin comprising:

a wafer defined into a plurality of islands;

at least one integrated circuit fabricated in or on the wafer;

at least one sensor element fabricated in or on each island and coupled to the integrated circuit;

a polymer layer disposed on the wafer and on the sensor element, the polymer layer providing mechanical support for the sensor element and islands; and a cavity defined in the island below each sensor element to provide thermal isolation from the island, while the sensor element remains supported by the polymer layer, where the integrated circuits comprise biasing or signal conditioning circuits adapted for the sensor elements among the integrated circuits provided in the wafer.

8. The sensor of claim 7 where the integrated circuit comprises a multiplexer for selectively accessing a plurality of the sensor elements on the skin.

9. The sensor of claim 4 where the second polymer layer comprises a Parylene C layer disposed as the second polymer layer on the opposing side.

10. A monolithic IC-integrated, flexible sensor skin comprising:

a flexible supporting skin;

a wafer defined into a plurality of islands and carried by the flexible supporting skin;

at least one integrated circuit fabricated in or on the wafer carried by the flexible supporting skin;

an integrated electrical coupling connected to the integrated circuit;

at least one integrated sensor element fabricated in or on at least one island during the same fabrication process as the integrated circuit, carried by the flexible supporting skin, and coupled to the integrated circuit through the integrated electrical coupling;

whereby the islands with at least one sensor element, and the integrated circuit coupled thereto form the IC-integrated, flexible sensor skin.

11. The IC-integrated, flexible sensor skin of claim 10 where the integrated circuit includes at least one gate and where the sensor element is fabricated in an integrated process with the gate of the integrated circuit.

12. The IC-integrated, flexible sensor skin of claim 10 where the skin is placed into contact with biological tissue and where the sensor element and integrated circuit in combination monitors a physiological parameter.

* * * * *

UNITED STATES PATENT AND TRADEMARK OFFICE
CERTIFICATE OF CORRECTION

PATENT NO. : 6,825,539 B2
DATED : November 30, 2004
INVENTOR(S) : Yu-Chong Tai and Yong Xu It is certified that error appears in the above-identified patent and that said Letters Patent is hereby corrected as shown below:

Column 1,
Line 12, insert -- The U.S. Government has certain rights in this invention pursuant to Grant No. EEC-9402726 awarded by the National Science Foundation and Grant No. N66001-97-C-8610 awarded by DARPA. --.

Signed and Sealed this

Third Day of January, 2006

JON W. DUDAS
*Director of the United States Patent and Trademark Office*